(12) United States Patent
Scheiner et al.

(10) Patent No.: US 6,321,122 B1
(45) Date of Patent: Nov. 20, 2001

(54) SINGLE PASS DEFIBRILLATION/PACING LEAD WITH PASSIVELY ATTACHED ELECTRODE FOR PACING AND SENSING

(75) Inventors: Avram Scheiner, Vadnais Heights; Curtis C. Lindstrom, Roseville; Robert S. Booker, III; Yayun Lin, both of St. Paul; Peter T. Kelley, Buffalo; John E. Heil, White Bear Lake; William Hsu, Circle Pines; Ronald W. Heil, Jr., Roseville, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/121,018

(22) Filed: Jul. 22, 1998

(51) Int. Cl.[7] .................................................. A61N 1/00

(52) U.S. Cl. ............................................................ 607/122
(58) Field of Search ..................................... 607/125, 122

(56) References Cited

U.S. PATENT DOCUMENTS

| | | |
|---|---|---|
| 3,614,955 | 10/1971 | Morowski . |
| 3,804,098 | 4/1974 | Friedman . |
| 3,866,615 | 2/1975 | Hewson ........................... 128/419 D |
| 3,926,197 | 12/1975 | Alley, III ........................ 128/419 PT |
| 3,942,536 | 3/1976 | Mirowski et al. . |
| 4,030,508 | 6/1977 | Thalen . |
| 4,030,509 | 6/1977 | Heilman et al. . |
| 4,106,512 | 8/1978 | Bisping . |
| 4,136,703 | 1/1979 | Wittkampf . |
| 4,154,247 | * 5/1979 | O'Neill ................................. 607/125 |
| 4,170,999 | 10/1979 | Allen et al. ........................... 128/419 |
| 4,217,913 | 8/1980 | Dutcher . |

(List continued on next page.)

FOREIGN PATENT DOCUMENTS

| | | |
|---|---|---|
| 2827595 | 5/1978 | (DE) . |
| 0573275 | 12/1993 | (EP) . |
| 0620024 | 10/1994 | (EP) . |
| 0813886 | 12/1997 | (EP) . |
| 0057877 | 8/1982 | (EP) ..................................... 607/121 |
| 0211166 | 2/1987 | (EP) .............................. A61N/1/05 |
| 0452278 | 10/1991 | (EP) .............................. A61N/1/05 |
| 0460324 | 12/1991 | (EP) .............................. A61N/1/05 |
| 0612538 | 8/1994 | (EP) .............................. A61N/1/05 |
| 0672431 | 9/1995 | (EP) .............................. A61N/1/05 |
| 2588758 | 4/1987 | (FR) .............................. A61N/1/05 |
| 2240721 | 8/1991 | (GB) . |
| 2032278 | 6/1980 | (GB) ............................ A61M/25/00 |
| 3-168161 | 7/1991 | (JP) . |
| 4-40966 | 2/1992 | (JP) . |
| 92/07616 | 5/1992 | (WO) . |
| 96/15665 | 11/1994 | (WO) .............................. A01N/1/05 |
| 89/06148 | 7/1989 | (WO) .............................. A61N/1/05 |

OTHER PUBLICATIONS

Fain, et al., "A New Internal Defibrillation Lead System: Intrapercardial Placement Without Thoracotomy", *Abstracts Circulation*, 76, Suppl. IV, 1839 (Oct. 1987).

(List continued on next page.)

*Primary Examiner*—Scott M. Getzow
(74) *Attorney, Agent, or Firm*—Schwegman, Lundberg, Woessner & Kluth, P.A.

(57) ABSTRACT

A single-pass endocardial lead electrode adapted for implantation on or about the heart and for connection to a system for monitoring or stimulating cardiac activity includes a lead body with a circumferential outer surface. The lead includes a first distal end electrode which has a first electrical conducting surface. The lead body also has a second electrode which has a second electrical conducting surface. The second electrode is adapted for positioning and fixation to the wall of the atrium of the heart. A passive fixation element may be used as part of the second electrode. The lead body also includes a curved portion which facilitates the positioning and passive fixation of the second electrode.

35 Claims, 6 Drawing Sheets

U.S. PATENT DOCUMENTS

| | | | |
|---|---|---|---|
| 4,270,549 | 6/1981 | Heilman . | |
| 4,291,707 | 9/1981 | Heilman et al. . | |
| 4,299,239 | 11/1981 | Weiss et al. | 127/785 |
| 4,311,153 | 1/1982 | Smits . | |
| 4,463,765 | 8/1984 | Gold . | |
| 4,548,203 | 10/1985 | Tacker, Jr. et al. . | |
| 4,559,951 | 12/1985 | Dahl et al. . | |
| 4,567,900 | 2/1986 | Moore . | |
| 4,567,901 | 2/1986 | Harris | 128/786 |
| 4,570,642 | 2/1986 | Kane et al. . | |
| 4,603,705 | 8/1986 | Speicher et al. . | |
| 4,624,265 | 11/1986 | Grassi . | |
| 4,624,266 | 11/1986 | Kane . | |
| 4,627,439 | 12/1986 | Harris . | |
| 4,633,880 | 1/1987 | Osypka et al. . | |
| 4,646,755 | 3/1987 | Kane . | |
| 4,649,937 | 3/1987 | DeHaan et al. . | |
| 4,649,938 | 3/1987 | McArthur . | |
| 4,662,377 | 5/1987 | Heilman et al. . | |
| 4,664,113 | 5/1987 | Frisbie et al. . | |
| 4,721,115 | 1/1988 | Owens | 128/713 |
| 4,727,877 | 3/1988 | Kallok . | |
| 4,784,161 | 11/1988 | Skalsky et al. . | |
| 4,799,486 | 1/1989 | DuFault . | |
| 4,799,493 | 1/1989 | DuFault . | |
| 4,817,608 | 4/1989 | Shapland et al. . | |
| 4,817,634 | 4/1989 | Holleman et al. . | |
| 4,819,661 | 4/1989 | Heil, Jr. et al. . | |
| 4,819,662 | 4/1989 | Heil, Jr. et al. . | |
| 4,827,932 | 5/1989 | Ideker et al. . | |
| 4,860,769 | 8/1989 | Fogarty et al. . | |
| 4,865,037 | 9/1989 | Chin et al. . | |
| 4,886,074 | 12/1989 | Bisping . | |
| 4,905,691 | 3/1990 | Rydell . | |
| 4,924,881 | 5/1990 | Brewer . | |
| 4,938,231 | 7/1990 | Milijasevic et al. . | |
| 4,944,300 | 7/1990 | Saksena . | |
| 4,953,551 | 9/1990 | Mehra et al. . | |
| 4,962,767 | 10/1990 | Brownlee | 128/786 |
| 4,967,766 | 11/1990 | Bradshaw . | |
| 4,971,070 | 11/1990 | Holleman et al. . | |
| 4,998,975 | 3/1991 | Cohen et al. . | |
| 5,016,645 | 5/1991 | Williams et al. . | |
| 5,016,646 | 5/1991 | Gotthardt et al. . | |
| 5,016,808 | 5/1991 | Heil, Jr. et al. . | |
| 5,020,544 | 6/1991 | Dahl et al. . | |
| 5,044,375 | 9/1991 | Bach, Jr. et al. . | |
| 5,050,601 | 9/1991 | Kupersmith et al. . | |
| 5,056,516 | 10/1991 | Spehr . | |
| 5,063,932 | 11/1991 | Dahl et al. . | |
| 5,076,285 | 12/1991 | Hess et al. . | |
| 5,083,562 | 1/1992 | de Coriolis et al. . | |
| 5,105,826 | 4/1992 | Smits et al. . | |
| 5,107,834 | 4/1992 | Ideker et al. . | |
| 5,111,811 | 5/1992 | Smits . | |
| 5,111,812 | 5/1992 | Swanson et al. . | |
| 5,129,404 | 7/1992 | Spehr et al. . | |
| 5,133,353 | 7/1992 | Hauser . | |
| 5,133,365 | 7/1992 | Heil, Jr. et al. . | |
| 5,152,299 | 10/1992 | Soukup . | |
| 5,165,403 | 11/1992 | Mehra . | |
| 5,174,289 | 12/1992 | Cohen | 128/419 PG |
| 5,174,303 | 12/1992 | Schroeppel . | |
| 5,203,348 | 4/1993 | Dahl et al. . | |
| 5,209,229 | 5/1993 | Gilli . | |
| 5,230,337 | 7/1993 | Dahl et al. . | |
| 5,259,394 | 11/1993 | Bens . | |
| 5,259,395 | 11/1993 | Li . | |
| 5,261,400 | 11/1993 | Bardy . | |
| 5,269,319 | 12/1993 | Schulte et al. . | |
| 5,271,417 | 12/1993 | Swanson et al. . | |
| 5,282,845 | 2/1994 | Bush et al. | 607/128 |
| 5,300,108 | 4/1994 | Rebell et al. | 607/127 |
| 5,300,110 | 4/1994 | Latterell et al. | 607/130 |
| 5,314,459 | 5/1994 | Swanson et al. | 607/122 |
| 5,324,327 | 6/1994 | Cohen | 607/122 |
| 5,342,414 | 8/1994 | Mehra | 607/127 |
| 5,344,439 | 9/1994 | Otten | 607/126 |
| 5,358,516 | 10/1994 | Myers et al. | 607/116 |
| 5,366,496 | 11/1994 | Dahl et al. | 607/132 |
| 5,374,286 | 12/1994 | Morris | 607/119 |
| 5,383,908 | 1/1995 | Sweeney et al. | 604/5 |
| 5,397,342 | 3/1995 | Heil, Jr. et al. | 607/129 |
| 5,405,373 | 4/1995 | Petersson et al. | 607/121 |
| 5,411,544 | 5/1995 | Mar et al. | 607/122 |
| 5,425,755 | 6/1995 | Doan | 607/119 |
| 5,425,756 | 6/1995 | Heil, Jr. et al. | 607/128 |
| 5,447,533 | 9/1995 | Vachon et al. | 607/120 |
| 5,447,534 | 9/1995 | Jammet | 607/127 |
| 5,456,706 | 10/1995 | Pless et al. | 607/122 |
| 5,456,708 | 10/1995 | Doan et al. | 607/127 |
| 5,476,501 | 12/1995 | Stewart et al. | 607/127 |
| 5,492,119 | 2/1996 | Abrams | 128/642 |
| 5,496,362 | 3/1996 | KenKnight et al. | 607/129 |
| 5,500,008 | 3/1996 | Fain | 607/5 |
| 5,514,174 | 5/1996 | Heil, Jr. et al. | 607/128 |
| 5,522,874 | 6/1996 | Gates | 607/127 |
| 5,531,780 | 7/1996 | Vachon | 607/120 |
| 5,534,022 | 7/1996 | Hoffmann et al. | 607/122 |
| 5,545,205 | 8/1996 | Schulte et al. | 607/123 |
| 5,554,178 | 9/1996 | Dahl et al. | 607/122 |
| 5,578,068 | 11/1996 | Laske et al. | 607/126 |
| 5,628,779 | 5/1997 | Bornzin et al. | 607/123 |
| 5,674,274 | 10/1997 | Morgan et al. | 607/123 |
| 5,755,761 | 5/1998 | Obino | 607/122 |
| 5,772,693 | 6/1998 | Brownlee | 607/123 |
| 5,776,072 | 7/1998 | Hsu et al. | 600/518 |
| 5,782,898 | 7/1998 | Dahl et al. | 607/119 |
| 5,885,221 | 3/1999 | Hsu et al. | 600/515 |
| 5,964,795 | 10/1999 | McVenes et al. | 607/122 |
| 6,055,457 | 4/2000 | Bonner | 607/126 |

OTHER PUBLICATIONS

Jones, D.L., et al., "Internal Cardiac Defibrillation in Man: Pronounced Improvement with Sequential Pulse Delivery to Two Different Lead Orientations", *Circulation,* vol. 73, No. 3, pp. 484–491 (Mar. 1986).

U.S. application No. 09/121,020, filed on Jul. 22, 1998 entitled "Single Pass Defibrillation/Pacing Lead with Passively Attached Electrode for Pacing and Sensing".

U.S. application No. 09/1231,006, filed Jul. 22, 1998 entitled "Single Pass Lead Having Retractable, Actively Attached Electrode For Pacing and Sensing".

U.S. application No. 09/121,019, filed Jul. 22, 1998 entitled "Single–Pass Endocardial Lead for Multi–Site Atrial Pacing".

U.S. application No. 09/121,288, filed on Jul. 22, 1998 entitled "High Impedance Electrode Tip".

U.S. application No. 09/120,824, filed on Jul. 22, 1998 entitled "Single Pass Lead System".

U.S. application No. 09/121,005, filed on Jul. 22, 1998 entitled "Single Pass Lead and System with Active and Passive Fixation Elements".

\* cited by examiner

SINGLE PASS DEFIBRILLATION/PACING LEAD WITH PASSIVELY ATTACHED ELECTRODE FOR PACING AND SENSING

RELATED APPLICATIONS

This patent application is related to an application entitled "SINGLE PASS LEAD HAVING RETRACTABLE, ACTIVELY ATTACHED ELECTRODE FOR PACING AND SENSING" which is assigned to a common assignee and is filed on a date even herewith. The related application is incorporated herein by reference.

FIELD OF THE INVENTION

The present invention relates to the field of leads for correcting arrhythmias of the heart. More particularly, this invention relates to a single lead which can simultaneously pace/sense and/or defibrillate two chambers of the heart.

BACKGROUND OF THE INVENTION

Electrodes implanted in the body for electrical cardioversion or pacing of the heart are well known. More specifically, electrodes implanted in or about the heart have been used to reverse (i.e., defibrillate or cardiovert) certain life threatening arrhythmias, or to stimulate contraction (pacing) of the heart, where electrical energy is applied to the heart via the electrodes to return the heart to normal rhythm. Electrodes have also been used to sense near the sinus node in the atrium of the heart and to deliver pacing pulses to the atrium. An electrode positioned in any chamber of the heart senses the electrical signals that trigger the heartbeat. Electrodes detect abnormally slow (bradycardia) or abnormally fast (tachycardia) heartbeats. In response to the sensed bradycardia or tachycardia condition, a pulse generator produces pacing or defibrillation pulses to correct the condition. The same electrode used to sense the condition is also used in the process of delivering a corrective pulse or signal from the pulse generator of the pacemaker.

There are four main types of pulses or signals which are delivered by a pulse generator. Two of the signals or pulses are for pacing the heart. First of all, there is a pulse for pacing the heart when it is beating too slowly. The pulses trigger the heart beat. These pulses are delivered at a rate to increase the abnormally low heart rate to a normal or desired level. The second type of pacing is used on a heart that is beating too fast. This type of pacing is called antitachycardia pacing. In this type of pacing, the pacing pulses are delivered initially at a rate much faster or slower than the abnormally beating heart until the heart rate can be returned to a normal or desired level. The third and fourth types of pulses are delivered through large surface area electrodes used when the heart is beating too fast or is fibrillating, respectively. The third type is called cardioversion. This is delivery of a relatively low energy shock, typically in the range of 0.5 to 5 joules, to the heart. The fourth type of pulse or signal is a defibrillation signal which is the delivery of a high energy shock, typically greater than 25 joules, to the heart.

Sick sinus syndrome and symptomatic AV block constitute the major reasons for insertion of cardiac pacemakers today. Cardiac pacing may be performed by the transvenous method or by electrodes implanted directly onto the epicardium. Most commonly, permanent transvenous pacing is performed using one or more leads with electrodes positioned within one or more chambers of the heart. The distal end of a lead, sometimes referred to as a catheter, may be positioned in the right ventricle or in the right atrium through a subclavian vein. The lead terminal pins are attached to a pulse generator which is implanted subcutaneously.

Some patients require a pacing system to detect and correct an abnormal heartbeat in both the atrium and ventricle which may have independent rhythms, as well as a defibrillation system to detect and correct an abnormally fast heart rate (tachycardia condition). In the past, a common practice for a patient having to pace both of these chambers would be to provide two different leads attached to the heart. One would be implanted for delivering pacing/sensing/ defibrillating to the ventricle and one to the atrium to both pace and sense.

Having two separate leads implanted within the heart is undesirable for many reasons. Among the many reasons are that the implantation procedure for implanting two leads is more complex and also takes a longer time when compared to the complexity and time needed to implant a single lead. In addition, two leads may mechanically interact with one another after implantation which can result in dislodgment of one or both of the leads. In vivo mechanical interaction of the leads may also cause abrasion of the insulative layer along the lead which can result in an electrical failure of one or both of the leads. Another problem is that as more leads are implanted in the heart, the ability to add other leads is reduced. If the patient's condition changes over time the ability to add leads is restricted. Two separate leads also increase the risk of infection and may result in additional health care costs associated with re-implantation and follow-up.

Because of these problems, catheters having electrodes for both pacing and sensing in both chambers of the heart on a single lead body have been used. These leads, known as single pass lead designs, have drawbacks since the single pass lead designs utilize "floating" electrodes or electrodes which are not attached to the endocardial wall of the heart. The catheter having the electrodes which forms the lead body is essentially straight. The electrode or electrodes may float or move slightly at a distance from the endocardial wall within the heart.

The portion of the lead positioned within the atrium of current single-pass endocardial leads has one or more electrodes which are incorporated into the lead body as an electrically conductive cylindrical or semicylindrical ring structure. In other words, the lead body is basically cylindrical and the one or more electrodes positioned within the atrium of the heart are cylindrical metal structures incorporated into the cylindrical lead body. The ring electrode structures do not allow for tissue ingrowth into the electrode to enhance electrode stabilization within the atrium. Since the location of the electrodes is not fixed against the atrial wall, the performance of these leads is more variable. In other words, variations with respect to electrical contact with the wall of the atrium results in suboptimal electrical sensing capability and pacing delivery capability. Typically, the pacing characteristics of a floating electrode are less desirable than the pacing characteristics associated with an electrode fixed to the endocardial wall of the heart. The performance of a lead using a floating electrode is poorer than a lead having electrodes which contact or are nearer the walls of the heart.

Another problem associated with the current straight single pass leads, is that these electrodes may be unable or less able to sense an arrhythmic condition. In addition, the applied voltage or current needed for pacing may be ineffective. Additional energy may have to be used to pace the heart thereby depleting energy from the battery of the pulse generator of the pacing system.

There is a real need for a single-pass transvenous pacing or defibrillation lead. A single-pass lead equipped with such an electrode arrangement would allow for better sensing capability and better pacing therapy to the heart. In addition, there is a need for a single-pass lead having an electrode for positioning within the atrium that allows for tissue ingrowth. Such an electrode would further enhance lead stabilization within the heart. There is also a need for a single-pass endocardial lead which has an electrode for placing within the right atrium of the heart that accommodates eluting anti-inflammatory drugs. There is still a further need for a single pass endocardial lead that is easier for a surgeon to implant.

SUMMARY OF THE INVENTION

A single-pass endocardial lead electrode adapted for implantation and for connection to a system for monitoring or stimulating cardiac activity includes a lead body with a circumferential outer surface. The lead includes a first distal end electrode or electrode pair which has a first electrical conducting surface. The lead body also has a second electrode or electrode pairs which has a second electrical conducting surface. The second electrode or electrode pair is adapted for positioning and fixation to the wall of the atrium of the heart. A passive fixation element is used as part of the second electrode or electrode pair. The lead body also includes a curved portion which facilitates the positioning and fixing of the second electrode or electrode pair. The curved portion has a radius near the natural radius of the atrium. The first and second electrode may be a single electrode or a bipolar pair. The curve in the lead body, which is positioned in the right atrium of the heart after implantation, positions the electrode closer to the wall of the atrium to enhance the sensing and pacing performance of the lead.

The electrical conducting surface of the second electrode has a relatively small diameter when compared to previous electrodes. The small diameter electrode results in superior electrical performance when compared to previous single-pass endocardial leads. The benefits include increased pacing impedance, increased P-wave signal amplitudes and decreased atrial pacing capture thresholds. The increased impedance lets the battery energy source last longer. The single-pass lead equipped with an atrial electrode capable of being fixed to the endocardial wall allows for better sensing capability and better current delivery to the heart. The second electrode may be placed on the outside of the curved portion of the lead body. The fixed atrial electrode enhances lead stabilization within the heart. The result is no need for two leads in the heart. The costs and complexity associated with implanting and follow-up care for the single pass lead is less than two separate leads.

DESCRIPTION OF THE PREFERRED EMBODIMENT

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1:
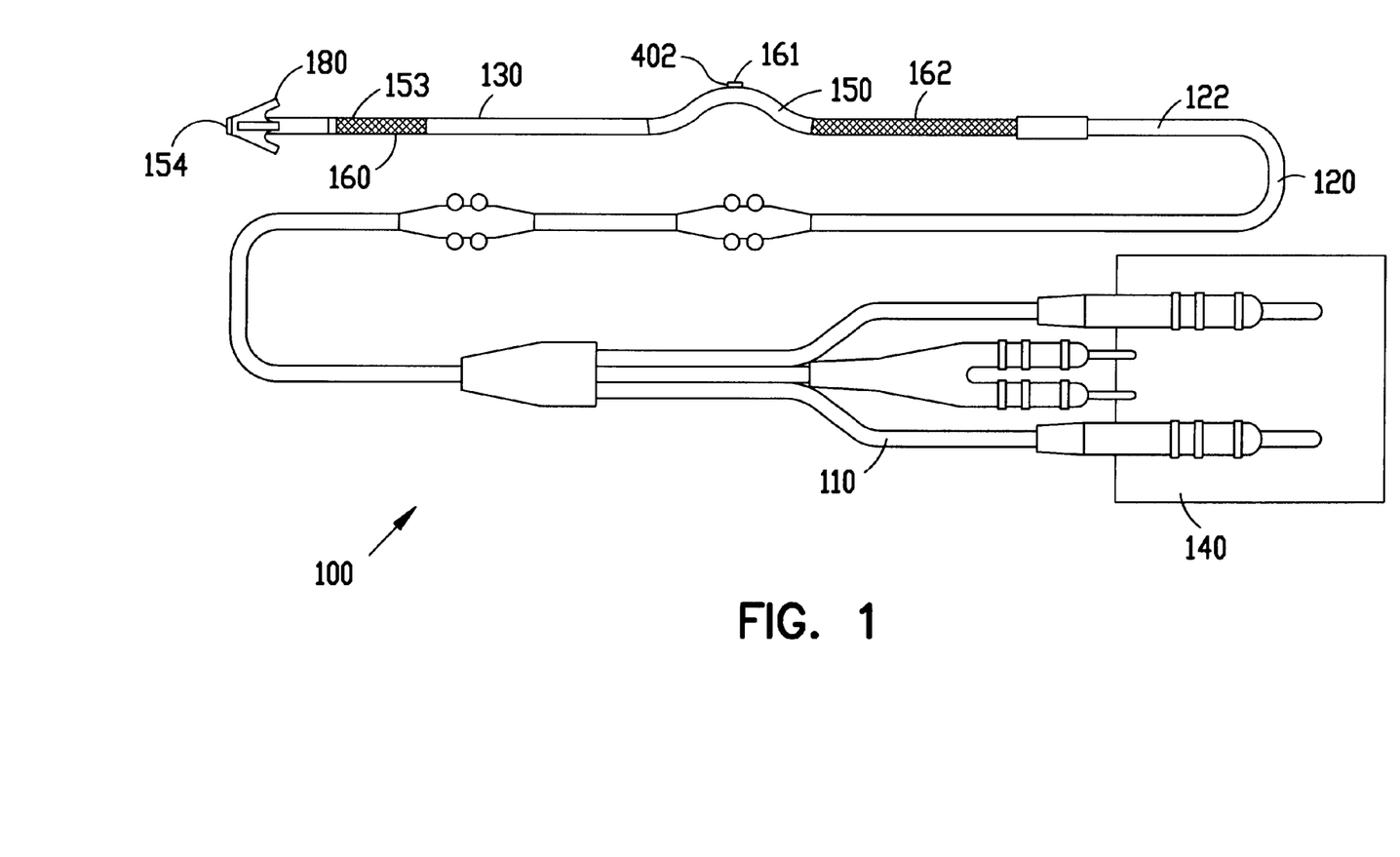
FIG. 1 is a side view of the dual chamber single pass lead with dual chamber sense pace and antitachyarrhythmic therapy for electrically stimulating the heart.

FIG. 1 is a side view of a lead 100 for delivering electrical pulses to stimulate the heart. The lead 100 is comprised of three basic portions, a connector terminal 110, an electrode end 130, and a portion 120 which interconnects the electrode end 130 and the connector terminal 110. All three of these portions, the interconnection portion 120, the electrode end 130 and the connector terminal 110 are constructed of conductive wires covered by a silicone rubber tubing which is biocompatible. Many times, the conductive wires within the silicone rubber tubing are referred to as the lead body 120. The connector terminal 110 electrically connects the various electrodes and conductors within the lead body to a pulse generator 140. The electrode end 130 is the portion of the lead 100 that includes electrodes and is positioned within the heart after implantation. The pulse sensor and generator 140 contains electronics to sense various electrical signals of the heart and also produce current pulses for delivery to the heart. The pulse sensor and generator 140 also contains electronics and software necessary to detect certain types of arrhythmias and to correct for them. The lead 100 shown in FIG. 1 is a single pass endocardial lead and is capable of producing all types of pulses, including pacing pulses, antitachycardia pulses, cardioversion pulses and defibrillation pulses. The lead terminal connector 110 provides for the electrical connection between the lead 100 and pulse generator 140.

The lead body 120 is cylindrical in shape. The lead body 120 is a tubing material formed from a biocompatible polymer for implantation, and preferably tubing made from a silicone rubber polymer. The silicone rubber polymer tubing contains several electrical conductors. The electrical conductors are made of a highly conductive, highly corrosion resistant material. Several separate electrical conductors are housed within the lead body 120. The connector terminal 110 connects the various electrodes and conductors within the lead body to the pulse generator 140.

After the lead 100 has been implanted, the electrode end 130 of the lead body 120 is situated predominantly within the heart. The electrode end 130 of the lead body 120 includes a curved or bias portion 150 and a straight portion 160. After implantation, bias portion 150 of the electrode end 130 will generally be located in the right atrium of the heart. Generally, portion 160 will be located in the right ventricle.

The electrode end 130 of the lead 100 has four electrodes. The lead 100 shown in FIG. 1 has two electrode pairs. One pair is located in the atrium and one pair in the ventricle. The first electrode 154 is provided at the farthest distal end of the lead for the purpose of delivering ventricular pacing therapy. The first electrode 154 is referred to as the RV pace/sense tip. A second electrode 153 is located proximate and proximal to electrode 154 and can be used as a counter electrode for 154 or as an electrode for defibrillation therapy. Electrode 153 is also known as the distal coil or the RV shock coil. The second electrode is actually a shocking coil and is much longer than the first electrode. A third electrode 161 is located at a more proximal position for the purpose of delivering atrial pacing therapy. Electrode 161 is also used for atrial sensing. Electrode 161 is also referred to as the atrial sense/pace electrode. This electrode 161 is intended to be passively attached to the atrial wall of the heart. A fourth electrode 162 is located proximate and proximal to electrode 161 and can be used with electrode 161 for atrial sensing/pacing and as counter to 153 as part of a defibrillation therapy system. Electrodes 153 and 162 are coils of a biocompatible metal or metal alloy such as, but not restricted to, platinum, or platinum/iridium. The coils are generally known as shocking coils and deliver large amounts of energy used in cardioversion and defibrillation. Electrode 162 is also referred to as the proximal coil or the SVC shock coil. The SVC shock coil 162 is positioned in the upper atrium or the superior vena cava. The atrial electrode 161 has a relatively small electrically active surface area. The advantages of this small surface area are high impedance for lower current drainage and a small lead cross section for ease of venous access and transport through the subclavian vein.

Figure 2:
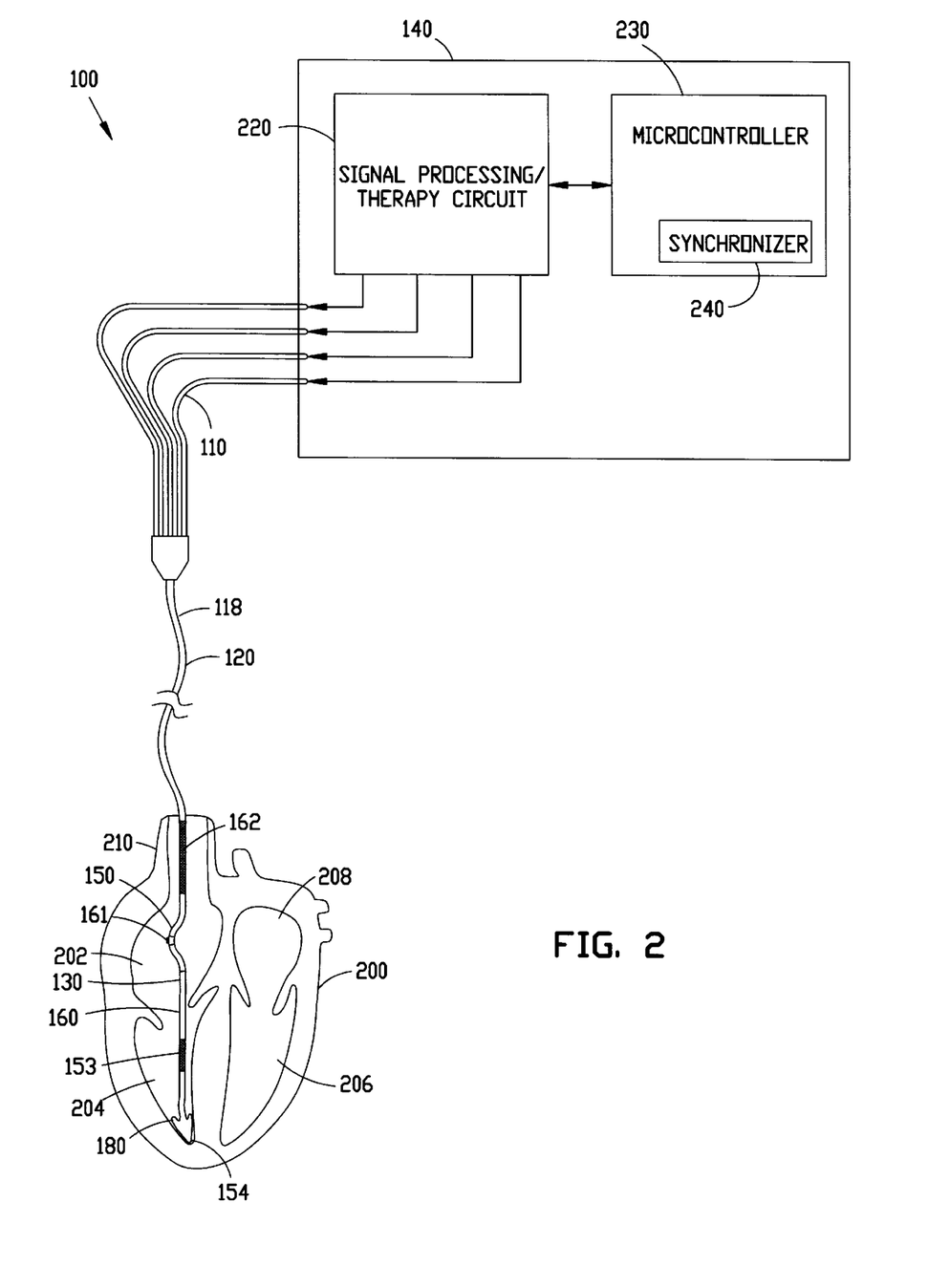
FIG. 2 is a side view of the single-pass endocardial lead for sensing and electrically stimulating the heart, positioned within the right ventricle and right atrium of the heart.

The shape of the curved portion 150 of the lead is important. FIG. 2 shows the lead 100 and, more specifically, the electrode end 130 positioned within a heart 200. The heart 200 includes four chambers which are the right atrium 202, the right ventricle 204, the left ventricle 206 and the left atrium 208. Also shown in FIG. 2 is the superior vena cava 210. The electrode end 130 of the lead 100 is positioned within the superior vena cava 210, the right atrium 202 and the right ventricle 204. The curved portion 150 of the lead 100 positions the atrial sense electrode 161 on the curved portion or biased section 150 closer to the wall of the heart in the right atrium 202. This enhances electrical performance as electrode 161 will be closer to the portion of the heart 200, namely the right atrium 202, where the signal will pass. In addition, the electrode 161 is positioned closer to the wall of the right atrium 202 such that passive fixation may be possible. If passive fixation is achieved, the electrode end 130 of the lead 100 will be more stably fixed within the heart 200. If the passive fixation is not achieved, at least the electrode 161 will be closer to the wall of the right atrium 202 so as to enhance the electrical sensing capability of that electrode. Also, near the electrode 154 are a set of tines 180. Tines 180 aid in positioning the electrode end 130 in the right ventricle 204 at the time of lead insertion. At the time of lead implantation, the distal electrode 154 is generally positioned in the right ventricle. Tines 180 are first needed to engage tissue structures which line the endocardial surface of the chamber 204. This engagement holds the lead in place when first implanted. Later, fibrous tissue grows over these tines 180 over time to produce an attachment to the wall of the heart in the right ventricle 204.

FIG. 2 also shows the lead terminal connector 110 and its connection into the pulse generator 140. The lead terminal connector 110 makes electrical connection with a signal processing/therapy circuit 220 which in turn is electrically connected to a microcontroller 230. Within the microcontroller 230 is a synchronizer 240. The signal processing/therapy circuit 220 determines the type of therapy that should be delivered to the heart 200. The microcontroller 230 controls the delivery of the therapy to the heart through the synchronizer 240. The synchronizer 240 times the delivery of the appropriate signal to the heart.

Figure 3:
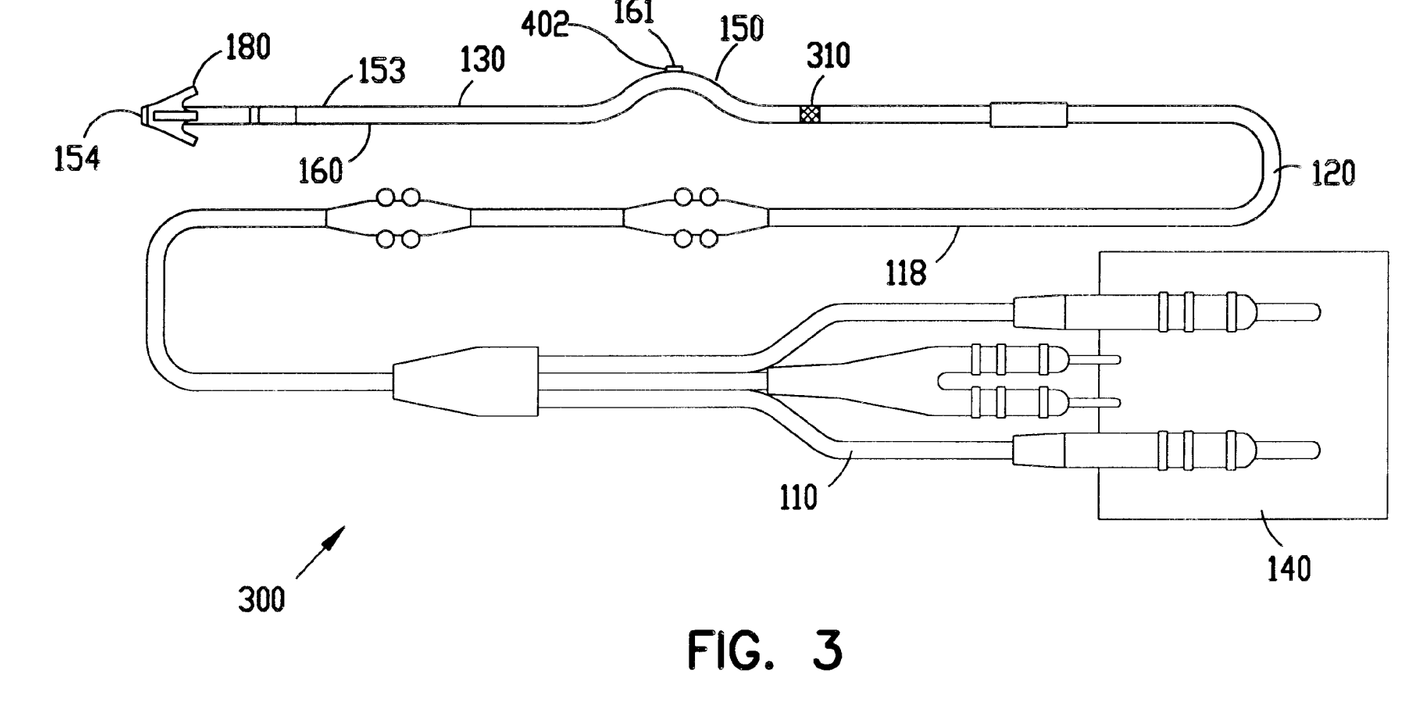
FIG. 3 is a view of a dual chamber single pass endocardial lead having a passive attachment element on the curved portion of the lead.

FIG. 3 shows a lead 300 used to treat a bradycardia condition. The lead 300 differs from the lead 100 in that there is no proximal or SVC shock coil, and no distal shock coil. The reference numerals associated with the lead 100 which describes similar parts have been used here for the purposes of simplicity. The lead 300 includes a distal or RV pace sense tip 154, an atrial sense electrode 161, and a ring electrode 310. The electrode end 130 of the lead 300 includes a straight portion 160 and a curved portion 150. The atrial sense electrode 161 is positioned on the portion 150. Portion 150 is curved. This allows the atrial sense electrode 161 to be positioned closer to the wall of the atrium of the heart. The atrial sense electrode 161 can also be provided with a means for passive fixation to the wall of the heart. In this unipolar application, the distal tip electrode 154 serves as the negative pole and the pulse sensor and generator 140 serves as the positive pole when a pacing pulse is delivered to the right ventricle of the heart. It should be noted that this is not the only possible unipolar arrangement, but that other unipolar arrangements are possible. Furthermore, it should be noted that a bipolar arrangement may also be used. Also, it should be noted that the electrode 161 is placed on the curved portion 150 of the lead 300. The placement is important in that the electrode 161 that is used for pacing and sensing points out in the direction of the bias of the curved portion 150. In other words, the electrode 161 is on the larger radius of the curved portion 150 of the lead. This assures that the distance between the electrode 161 and the wall of the atrium 202 is minimized. This also maximizes the possibility that the electrode 161 will become passively fixed to the wall of the heart. The outside surface of the curved portion 150 of the lead 300 can be textured to further enhance the passive fixation of the lead 161 to the heart.

The ring electrode 310 is also placed a selected distance from the electrode 161. The ring electrode 310 has the opposite polarity of the electrode 161. The ring electrode 310 is placed so that it is near the superior vena cava of the heart when the lead 300 is placed in the heart. The electrodes 310 and 161 are used as a bipolar pair for sensing and pacing. The lead 300 is a single pass lead that can be used for both sensing a bradycardia condition and treating it by pacing.

Figure 4:
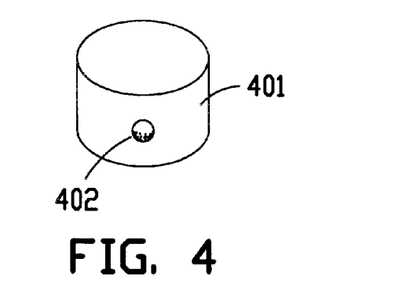
FIG. 4 is a perspective view of the atrial electrode portion of the lead showing a passive attachment element for attachment to the atrial wall of the heart.

FIGS. 4–11 further detail certain elements of the passive fixation single pass electrode used as electrode 161. FIG. 4 shows a conductive ring made of a highly conductive, and highly corrosion resistant, material such as an alloy of platinum-iridium. The ring 401 includes a small porous tip electrode 402. The ring 401 is electrically insulated from body fluids. The porous tip electrode is electrically active and in contact with body fluids and tissue. The active porous tip electrode 402 includes a screen of porous conductive material such as the alloy of platinum and iridium. Over time, the tissue encapsulation grows into the screen made of a platinum-iridium alloy to attach the electrode or electrodes to the endocardial wall of the heart. The electrode 161 has a nominal radius of 0.04 inches (1 mm). The advantage of this small radius is ease of venous access and high impedance for conserving pacing energy. Saving energy makes the battery used to power the pulse generator 140 last longer.

Figure 5:
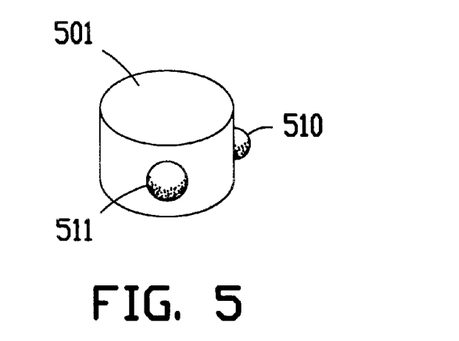
FIG. 5 is a side view of another embodiment of the electrode for passive attachment to the atrial wall of the heart.

FIG. 5 shows another passive fixation electrode. FIG. 5 shows a conductive ring 501 made of a highly corrosion-resistant material such as an alloy of platinum and iridium. The ring includes two small porous tip electrodes 510 and 511. The ring 501 is electrically insulated from body fluids. The porous tip electrodes 510 and 511 are electrically active and in contact with body fluids. The active porous tip electrodes 510 and 511 each include a screen of porous conductive material made of the highly corrosion-resistant alloy of platinum and iridium. As with the electrode shown in FIG. 4, tissue encapsulation grows into the screen on the tips 510 and 511 to attach the electrode to the endocardial wall of the heart.

Figure 6:
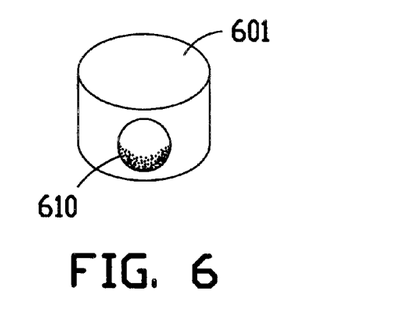
FIG. 6 is a side view of another embodiment of the electrode for passive attachment to the atrial wall of the heart.

FIG. 6 shows another passive fixation element associated with the electrode 161. FIG. 6 shows a conductive ring 601 again made of a highly conductive corrosion-resistant material. The ring 601 includes a porous tip electrode 610. The ring 601 is electrically insulated from body fluids. The porous tip electrode 610 is electrically active and in contact with body fluids. The porous tip 610 in FIG. 6 is larger than the porous tip 402 shown in FIG. 4. The porous tip 610 is made of corrosion-resistant material and is a screen. When the porous tip 610 lays against the endocardial wall of the heart, the tissue of the heart encapsulates and grows into the screen to passively attach the electrode to the heart.

Figure 7:
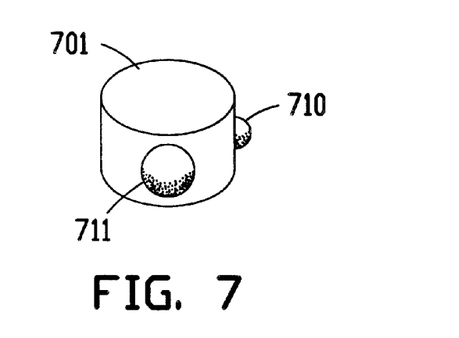
FIG. 7 is a side view of another embodiment of the electrode for passive attachment to the atrial wall of the heart.

FIG. 7 shows a variation of the electrode shown in FIG. 6. FIG. 7 shows a conductive ring 701 also made of highly conductive material. The conductive ring 701 includes a first porous tip 710 and a second porous tip 711. The ring 701 is electrically insulated from body fluids. The porous tip electrodes 710 and 711 are electrically active and in contact with body fluids. The porous tips are also made of highly corrosion-resistant material. Like the previous conductive rings shown, the tissue of the heart encapsulates and grows into the porous screen in order to provide passive attachment of the electrode to the endocardial wall of the heart.

Figure 8:
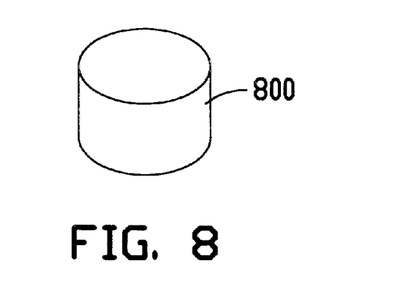
FIG. 8 is a side view of another embodiment of the electrode for passive attachment to the atrial wall of the heart.

FIG. 8 shows that a smooth ring 800 can also be used as the main element of the electrode 161 in the curved portion 150 of the lead 100. The smooth ring is made of a corrosion-resistant material that is highly conductive. All of the ring can be exposed or a portion of it can be masked or insulated, so that portion is nonconductive.

Figure 9:
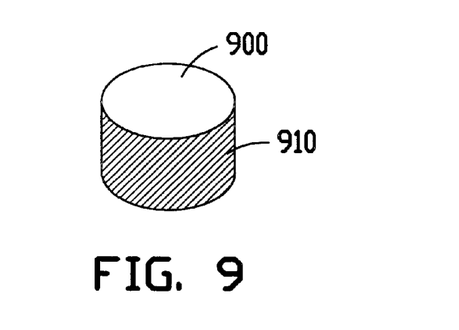
FIG. 9 is a side view of another embodiment of the electrode for passive attachment to the atrial wall of the heart.

FIG. 9 shows another variation and includes a ring 900. In FIG. 9, surface 910 is comprised of layers of conductive mesh or other porous materials attached to the ring 900. The layers of conductive mesh create an active surface for pacing and sensing and a layer for enhanced tissue ingrowth. Alternatively, texturization or other surface treatment could be applied to ring 900 to enhance tissue ingrowth.

Figure 10:
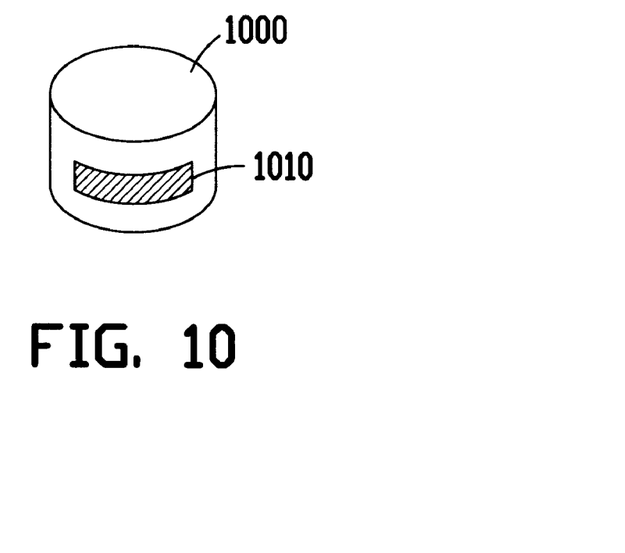
FIG. 10 is a side view of another embodiment of the electrode for passive attachment to the atrial wall of the heart.

FIG. 10 shows a modified raised ridge type of electrode. In this particular application, the layers of conductive porous material are deposited on a thin band rather than across the entire width of the ring. FIG. 10 shows a ring 1000 made of highly conductive material insulated from body fluids. The thin band is electrically active. The remaining portion of the ring 1000 is insulated. Attached to the ring is a raised ridge 1010. All of the ring 1000 can be exposed or a portion of it can be masked or insulated so that portion is nonconductive.

Figure 11:
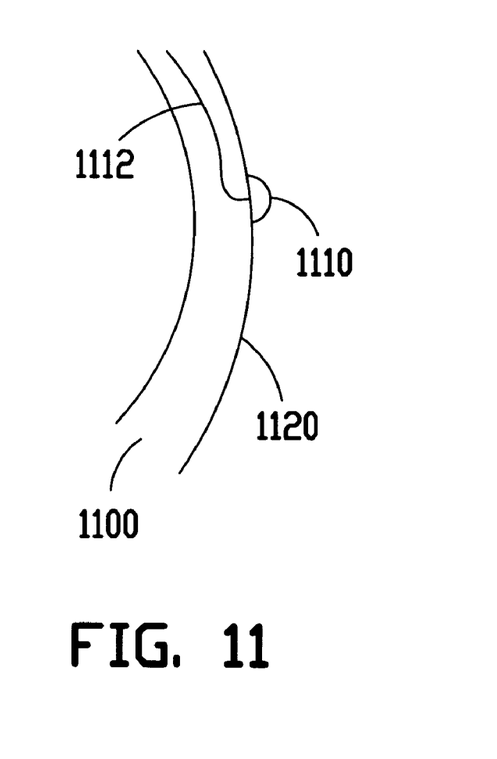
FIG. 11 is a side view of a portion of a lead body showing an electrode for passive attachment to the atrial wall of the heart.

FIG. 11 shows an portion of a lead 1100 which includes a porous tip type of electrode 1110 (like those shown in FIGS. 4 and 5) which is not mounted on a ring. The porous tip electrode 1110 is placed in either a straight or curved portion of the lead. The porous tip electrode 1110 is placed directly into the surface of the lead. An electrical conductor 1112 is attached to the electrode. The surface of the lead near the electrode 1120 may be textured to enhance the ability of the lead to become passively fixed to the wall of the heart.

Figure 12:
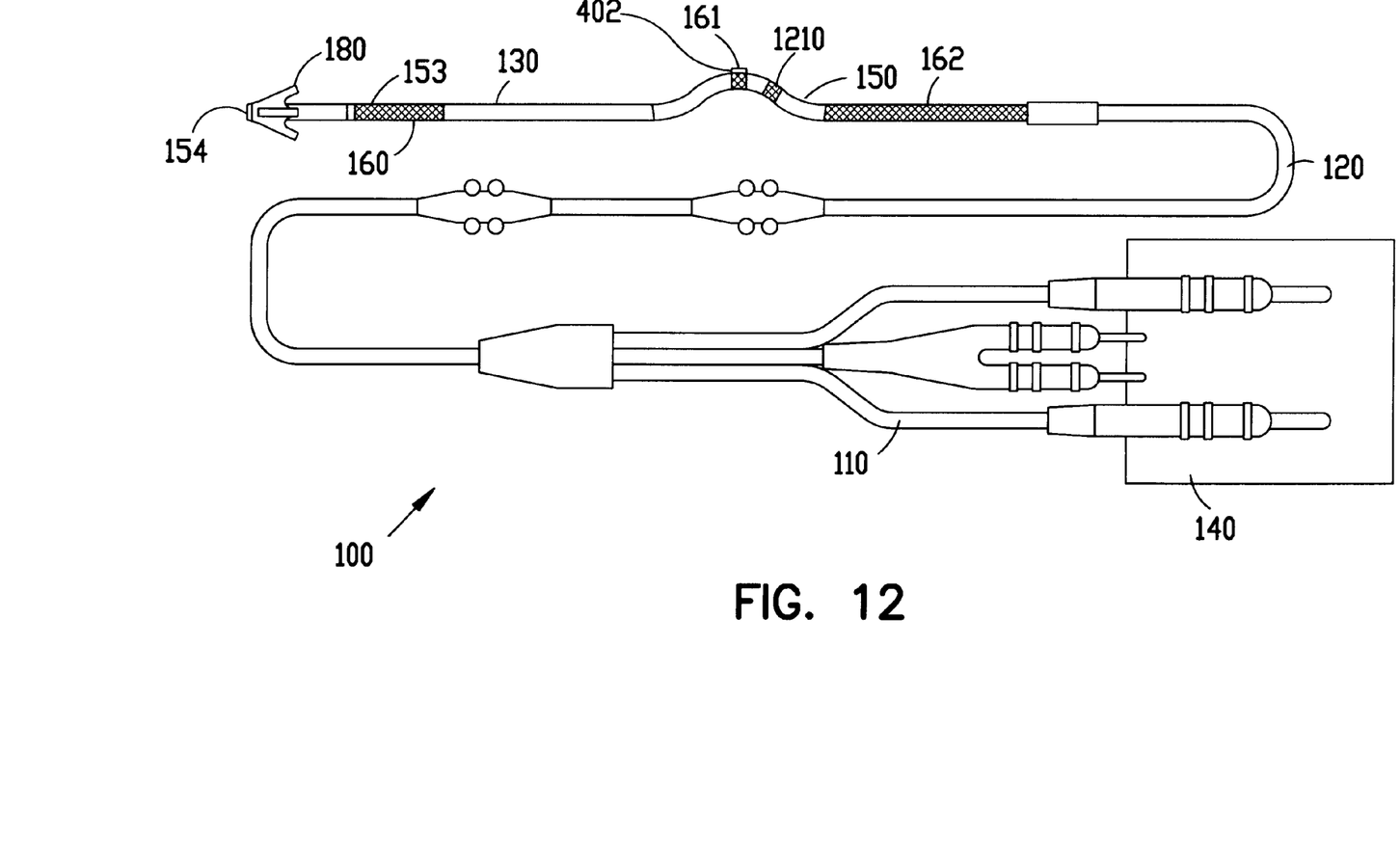
FIG. 12 is a side view of the dual chamber single pass lead with dual chamber sense pace and antiarrhythmic therapy for electrically stimulating the heart.

FIG. 12 is a side view of the dual chamber single pass lead with dual chamber sense pace and antiarrhythmic therapy for electrically stimulating the heart. FIG. 12 is similar to the lead shown in FIG. 1. As a result, the common elements will not be discussed here since reference may be had to the discussion of FIG. 1 above. The main difference between the lead shown in FIG. 1 and the lead shown in FIG. 12 is the electrode 1210. This is a fifth electrode on the lead. The electrode 1210 is positioned on the lead so that there are two sensing electrodes, 161 and 1210 in the atrium of the heart to enhance the sensing capability of this lead.

It should be noted that even though various rings are shown in FIGS. 4–10, the pacing and the sensing tip can be mounted to the curved portion 150 of the lead 100 or the lead 300 without a ring. In this instance, a tip would form the electrode 161 which is used as an atrial sense electrode. Once again, it should also be pointed out that the pacing and sensing tip points out in the direction of the bias or is on the portion of the lead body that is closest to the atrial wall of the heart. This positioning facilitates the electrical performance of the electrode 161.

It is contemplated that slight variations in the design could be used for a particular application as required. One such variation would be the provision of steroid elution from any of the electrodes 153, 154, 161 and 1210. Drug elution, typically steroid, can be provided by using one or more of the drug-releasing technologies such as sleeves or collars positioned in close proximity to the electrodes or by the use of internalized drug-containing plugs. An example of the composition of at least one collar is dexamethasone acetate in a simple silicone medical adhesive rubber binder or a steroid-releasing plug similarly fabricated.

The shape of the curved or bias portion 160 facilitates the placement of the atrial electrode against the atrial wall during implantation. The shape of the electrode end 130 will also be approximately the same before implantation as after implantation and the result will be that the shape reduces the nominal residual stresses in the lead body 100.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A lead adapted for implantation in, on or about the heart and for connection to a system for monitoring or stimulating cardiac activity, said lead comprising:

a lead body having a proximal end and a distal end, and a curved portion at a selected distance from the distal end of the lead body;

a first electrode attached to the lead body at the distal end of the lead body for contact with a first chamber of the heart; and a second electrode attached to the lead body, the second electrode comprising an electrically conductive ring positioned a distance from the first electrode on the curved portion of the lead body to facilitate attachment of the second electrode to a second chamber of the heart, the second electrode including a passive fixation element.

2. The lead as recited in claim 1, wherein the first chamber of the heart is the right ventricle of the heart and wherein the second chamber of the heart is the right atrium.

3. The lead as recited in claim 2, wherein the second electrode comprises a porous ring.

4. The lead as recited in claim 1, wherein the curved portion has a radius smaller than the radius associated with the inner wall of the atrium of the heart.

5. The lead as recited in claim 1, further comprising:
a third electrode positioned near the second electrode, said lead adapted for pacing and defibrillation of the heart.

6. The lead as recited in claim 1, further comprising:
a third electrode positioned near the first electrode; and
a fourth electrode positioned near the second electrode, said lead adapted for pacing and defibrillation of the heart.

7. The lead as recited in claim 6, wherein the third electrode positioned near the first electrode is a shocking coil.

8. The lead as recited in claim 6, wherein the fourth electrode positioned near the second electrode is a shocking coil for positioning near the superior vena cava.

9. The lead as recited in claim 8, further comprising a fifth electrode positioned near the second electrode, said fifth electrode used for atrial sensing within the atrium of the heart.

10. The lead as recited in claim 1, wherein the outside of the lead body includes a textured portion for passive fixation of the lead to the heart.

11. The lead as recited in claim 10, wherein the textured portion of the lead body is near the second electrode.

12. The lead as recited in claim 1, the lead body defined in part by a first longitudinal axis;
and the second electrode protruding outwardly from the lead body, said second electrode defined in part by a second longitudinal axis, where the first longitudinal axis is disposed transverse to the first longitudinal axis.

13. The lead as recited in claim 12, wherein the curved portion is disposed away from the lead body in a first direction, and the second electrode protrudes outwardly toward the first direction.

14. The lead as recited in claim 12, wherein the ring electrode includes at least one small porous tip electrode disposed on a side surface of the ring electrode.

15. The lead as recited in claim 12, wherein the ring electrode comprises a smooth ring.

16. The lead as recited in claim 12, wherein the ring electrode includes two or more layers of conductive mesh attached thereto.

17. The lead as recited in claim 12, wherein the ring electrode includes one or more layers of conductive mesh attached on a side surface of the ring electrode, where the layers are deposited on a thin band.

18. The lead as recited in claim 12, wherein the first electrode has opposite polarity than the second electrode.

19. The lead as recited in claim 1, wherein the second electrode is a porous ring having a diameter substantially the same as the lead body.

20. The lead as recited in claim 19, wherein the second electrode comprises a porous ring.

21. The lead as recited in claim 1, wherein the second electrode further comprises a plurality of raised ridges on said ring.

22. The lead as recited in claim 1, wherein the ring is partially masked.

23. A lead adapted for endocardial implantation on or about the heart and for connection to a system for monitoring or stimulating cardiac activity, said lead comprising:
a lead body having a proximal end and a distal end;
a first electrode attached to the distal end of the lead body; and
a second electrode attached to the lead body a selected distance away from the first electrode, said lead body formed with a curve therein to facilitate positioning of the second electrode within the heart, the second electrode further comprising a passive fixation element wherein the second electrode includes an electrically conductive ring element.

24. The lead adapted for endocardial implantation as recited in claim 23, wherein the first electrode is positioned within one chamber of the heart and the second electrode is positioned within another chamber of the heart.

25. The lead adapted for endocardial implantation as recited in claim 23, wherein the electrically conductive ring has a diameter substantially the same as the lead body.

26. The lead as recited in claim 23, wherein the lead body includes a textured portion positioned near the second electrode.

27. A system for delivering signals to the heart, said system comprising:
an electronics system further comprising:
a cardiac activity sensor; and
a signal generator which produces signals to stimulate the heart; and
a lead adapted for endocardial implantation on or about the heart, and for connection to the electronics system, said lead comprising:
a lead body having a proximal end and a distal end, and a curved portion at a selected distance from the distal end of the lead body;
a first electrode attached to the lead body; and
a second electrode attached to the lead body, said first electrode at the distal end of the lead body for contact with a first chamber of the heart and said second electrode positioned a distance from the first electrode on a curved portion of the lead body to facilitate attachment of the second electrode to the second chamber of the heart, said second electrode further comprising a passive fixation element
wherein the second electrode includes an electrically conductive ring element.

28. A lead comprising:
a lead body extending from a proximal end to a distal end, the lead body having a curved portion at a selected distance from the distal end of the lead body, the lead body defined in part by a first longitudinal axis;
a first electrode disposed at the distal end of the lead body;
a second electrode attached to the lead body, said second electrode positioned a predetermined distance from the first electrode to facilitate attachment of the second electrode to a second chamber of the heart, where the second electrode protrudes outwardly from the lead body, said second electrode comprising a ring electrode defined in part by a second longitudinal axis, where the first longitudinal axis is disposed transverse to the first longitudinal axis; and wherein the ring electrode includes at least one small porous tip electrode.

29. The lead as recited in claim 28, wherein the ring electrode includes a first small porous tip electrode and a second small porous tip electrode.

30. The lead as recited in claim 29, wherein the ring electrode has an outer surface, and the first small porous tip electrode and the second small porous tip electrode are disposed on the outer surface 90 degrees from one another.

31. The lead as recited in claim 28, wherein the ring electrode is defined by a first height and the at least one small porous tip electrode is defined in part by a first diameter, and the first diameter is greater than 50% of the first height.

32. A lead comprising:

a lead body extending from a proximal end to a distal end, the lead body having a curved portion at a selected distance from the distal end of the lead body, the lead body defined in part by a first longitudinal axis;

a first electrode disposed at the distal end of the lead body;

a second electrode attached to the lead body, said second electrode positioned a predetermined distance from the first electrode to facilitate attachment of the second electrode to a second chamber of the heart, where the second electrode protrudes outwardly from the lead body, said second electrode comprising a ring electrode defined in part by a second longitudinal axis, where the first longitudinal axis is disposed transverse to the first longitudinal axis; and wherein the ring electrode includes one or more layers of conductive mesh attached thereto.

33. A lead comprising:

a lead body extending from a proximal end to a distal end, the lead body having a curved portion at a selected distance from the distal end of the lead body, the lead body defined in part by a first longitudinal axis;

a first electrode disposed at the distal end of the lead body;

a second electrode attached to the lead body, said second electrode positioned a predetermined distance from the first electrode to facilitate attachment of the second electrode to a second chamber of the heart, where the second electrode protrudes outwardly from the lead body, said second electrode comprising a ring electrode defined in part by a second longitudinal axis, where the first longitudinal axis is disposed transverse to the first longitudinal axis; and wherein the ring electrode includes one or more layers of conductive mesh attached thereto, where the layers are deposited on a thin band.

34. The lead as recited in claim 33, wherein the thin band is raised from an outer surface of the ring electrode.

35. The lead as recited in claim 33, wherein the ring electrode is defined by a first portion comprising the thin band and a second portion comprising a remaining portion of the ring electrode, where the first portion is electrically active and the second portion is insulated.

* * * * *

UNITED STATES PATENT AND TRADEMARK OFFICE
CERTIFICATE OF CORRECTION

PATENT NO. : 6,321,122 B1
DATED : November 20, 2001
INVENTOR(S) : Scheiner et al.

It is certified that error appears in the above-identified patent and that said Letters Patent is hereby corrected as shown below:

Column 1,
Line 11, after "reference." insert -- This patent application is also related to U.S. Application No. 09/121,020, which is assigned to a common assignee and was filed on July 22, 1998. --.

Signed and Sealed this

Thirteenth Day of August, 2002

Attest:

JAMES E. ROGAN
Attesting Officer
Director of the United States Patent and Trademark Office